(12) United States Patent
Takahashi et al.

(10) Patent No.: US 6,658,884 B2
(45) Date of Patent: *Dec. 9, 2003

(54) REFRIGERATOR

(75) Inventors: Yasuyuki Takahashi, Oizmi-machi (JP); Kiyotaka Nagao, Oizmi-machi (JP); Toshihide Hasegawa, Oizmi-machi (JP); Motoyuki Murakoso, Nitta-machi (JP)

(73) Assignee: Sanyo Electric Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/155,792

(22) Filed: May 24, 2002

(65) Prior Publication Data

US 2002/0174674 A1 Nov. 28, 2002

(30) Foreign Application Priority Data

May 24, 2001 (JP) ........................... 2001-155940
May 24, 2001 (JP) ........................... 2001-155944
May 24, 2001 (JP) ........................... 2001-155947

(51) Int. Cl.$^7$ ............................. F25D 23/00; F24F 3/16
(52) U.S. Cl. ............................. 62/264; 62/78
(58) Field of Search ......................... 62/264, 78; 96/15, 96/16, 74

(56) References Cited

U.S. PATENT DOCUMENTS

| | | | | |
|---|---|---|---|---|
| 4,909,040 A | * | 3/1990 | Feltrin | 62/78 |
| 4,955,208 A | * | 9/1990 | Kawashima et al. | 62/264 |
| 5,901,564 A | * | 5/1999 | Comeau, II | 62/264 |
| 2003/0019222 A1 | * | 1/2003 | Takahashi et al. | 62/131 |

FOREIGN PATENT DOCUMENTS

| | | | | |
|---|---|---|---|---|
| JP | 07270043 A | * | 10/1995 | F25D/23/00 |
| JP | 11311469 A | * | 11/1999 | F25D/17/08 |

* cited by examiner

Primary Examiner—Chen Wen Jiang
(74) Attorney, Agent, or Firm—J.C. Patents

(57) ABSTRACT

A refrigerator is divided into a storage compartment and an air duct in a thermal insulating housing. The cold air for use of the thermal exchange with a cooler in the duct circulates in the storage compartment by a fan. The refrigerator has an ultraviolet ray irradiating device capable of irradiating ultraviolet rays. The ultraviolet ray irradiating device is installed at the inflow side of cooler, but separated from the cooler, so that the ultraviolet rays irradiate the duct by the ultraviolet ray irradiating device. Therefore, various germs such as bacteria or molds in the refrigerator can be prevented from growth, and the refrigerator can be deodorized.

19 Claims, 9 Drawing Sheets

REFRIGERATOR

CROSS-REFERENCE TO RELATED APPLICATION

This application claims the priority benefit of Japanese application serial no. 2001-155944, filed on May 24, 2001 and 2001-155947, filed on May 24, 2001 and 2001-155940 filed on May 24, 2001.

BACKGROUND OF THE INVENTION

1. Field of the Invention

This invention relates in general to a refrigerator that is configured with a storage compartment and a duct in a thermal insulating housing. In the storage room, cold air, which performs thermal exchange with a cooler installed in the air duct, circulates by a fan.

2. Description of Related Art

Conventionally, a refrigerator is made of thermal insulating housing, in which foam thermal insulating material such as polyurethane foam is filled by an in-situ foaming method between an external housing made of steel plate and an interior housing made of hard synthetic resin. The thermal insulating housing is divided to form a storage compartment, including a freezer compartment, a cold storage compartment and a vegetable compartment etc.

Additionally, a mechanical room is divided from the thermal insulating housing to be formed at the lower portion of the thermal insulating housing. In the mechanical room, a compressor forming a cooling device, a condenser, and a fan for the condenser etc are installed therein. The cooling device and a cooler, constituting a freezing cycle, are vertically arranged behind the back surface of the storage compartment. A fan for the cooler is installed above the cooler. A partition plate is formed in front of the cooler and the fan, and an air duct is formed between the partition plate and the back wall of the thermal insulating housing.

By operating the compressor of the cooling device and the fan, the cold air cooled in the air duct is blown to the storage compartment. In this way, the freezer compartment in the storage compartment is cooled to a freezing temperature, such as $-20°$ C., and additionally, the cold storage compartment in the storage compartment is maintained at a cold temperature such as $+5°$ C. In the vegetable compartment, foods such as vegetables that cannot become dry are reserved at a proper temperature.

As the foods etc are stored in the storage compartment of the refrigerator, various germs such as bacteria and molds adhere on the surface of eggs etc and diffuse in the storage compartment because of the cold air circulating in the storage compartment. These germs will adhere to other foods. In addition, the cold air containing the germs will return to the air duct, so that the germs will also adhere to the cooler and the cooler fan in the air duct.

As a result, germs, such as bacteria or molds, grow in the refrigerator, which is the reason that the stored foods etc spoil quickly and causes a problem of malodor.

Therefore, conventionally, a disinfection device and/or deodorization device is installed in the refrigerator. In such a device, an ultraviolet ray discharging lamp is generally used. It is well known that floating germs are disinfected by ultraviolet rays and a light catalyst is installed within an irradiating range of the ultraviolet rays to deodorize. Additionally, it is also well known that if the wavelength of the ultraviolet rays includes a range below 185 nm, ozone can be generated so that the disinfection and the deodorization can be performed by the ozone.

SUMMARY OF THE INVENTION

According to the foregoing description, an object of this invention is to provide a refrigerator having a suitable structure to achieve the above issues.

For example, when such a device is installed in the refrigerator, it is common for the device to be installed within the circulating passage of the cold air. It is a good idea to arrange the device at the cooler, the position where the cold air circulates. However, in general, as the temperature reduces, the illuminating efficiency of the discharging lamp reduces. Therefore, it is another object to provide a refrigerator capable of suppressing the efficiency of the discharging lamp from being decreased and capable of performing superior disinfection and deodorization.

According to the objects mentioned above, the invention provides a refrigerator, comprising: a cooler arranged at an upper portion from a middle of an innermost of a cold temperature area; an air duct located at the innermost of a cold temperature area and below the cooler, for returning cold air to the cooler; and a discharging lamp, for creating ultraviolet rays and irradiating the ultraviolet rays to the air duct. In this way, the discharging lamp is arranged away from the cooler, so that the reduction of illumination efficiency due to the low temperature can be suppressed.

The invention further provides a refrigerator, comprising: a first cooler for cooling a cold temperature area and being arranged at an upper portion from a middle of an innermost of a cold temperature area; a second cooler for cooling a freezing temperature area; an air duct located at the innermost of a cold temperature area and below the cooler, for returning cold air to the cooler; and a discharging lamp, for creating ultraviolet rays and irradiating the ultraviolet rays to the air duct. In this manner, because the discharging lamp is arranged away from the cooler, the reduction of the illuminating efficiency due to the low temperature can be suppressed.

The invention further provides a refrigerator, comprising: a thermal insulating housing, formed in the refrigerator, and a storage compartment and an air duct are divided therein; a cooler, formed in the air duct, using thermal exchange to cool cold air in the air duct; a fan, for circulating the cold air cooled by the cooler, in the storage compartment; and an ultraviolet ray irradiating device, having a first surface capable of irradiating ultraviolet rays and a second surface capable of irradiating visible light. Due to the ultraviolet ray irradiating device, the ultraviolet rays irradiate the air duct and visible light irradiates the storage compartment. In this way, the ultraviolet ray irradiating device can also serve as an indicator of illuminating status in the storage compartment. In addition, the ultraviolet ray irradiating device can disinfect the circulating cold air, the surface of the air duct and the devices installed in the air duct.

In the above refrigerator, a fluorescent material can be formed on the second surface capable of irradiating visible light. Therefore, the ultraviolet rays can be converted to visible light.

The above refrigerator can further comprise a partition plate for dividing the storage compartment and the air duct. The ultraviolet ray irradiating device is installed on the partition plate, so that the first surface capable of irradiating ultraviolet rays faces the air duct, and the second surface capable of irradiating visible light faces the storage room. Therefore, the structure can be simplified and the cost can be reduced.

Moreover, in the above refrigerator, the ultraviolet ray irradiating device is capable of being detachably installed from one side of the storage compartment. In this way, the maintenance for the ultraviolet ray irradiating device can be easily done at the side of the storage compartment.

In addition, the ultraviolet ray irradiating device is a plane-type lamp, and installed along a surface of the partition plate. Accordingly, the installation space of the ultraviolet ray irradiating device can be reduced, and the space efficiency can be increased. Because the storage volume of the storage compartment is not reduced and the circulation of the cold air in the air duct and the storage compartment is not blocked, the cooling efficiency can be increased.

In the above refrigerator, the surface of the air duct where the ultraviolet rays from the ultraviolet ray irradiating device irradiate thereon can be made of a metal material. Accordingly, it can prevent the surface of the air duct in advance from damage resulting from the ultraviolet rays.

The invention further provides a refrigerator, comprising: a thermal insulating housing, formed in the refrigerator, and a storage compartment and an air duct are divided therein; a cooler, formed in the air duct, for use of a thermal exchange with the cooler to cool a cold air in the air duct; a fan, for circulating the cold air cooled by the cooler, in the storage compartment; and an ultraviolet ray irradiating device, capable of irradiating ultraviolet rays. The ultraviolet ray irradiating device is installed at the inflow side of the cooler but separated from the cooler, so that ultraviolet rays irradiate the air duct from the ultraviolet ray irradiating device. In this way, the inside of the air duct can be easily disinfected. Additionally, in the air duct, the circulating cold air and the inner wall of the air duct can be disinfected, and the devices installed in the air duct can be also disinfected. Therefore, various germs such as the bacteria or the molds can be prevented from growing and malodor can be prevented from occurring.

In the above refrigerator, the fan is formed in the air duct and at an outflow side of the cooler. Because the fan is located at an opposite position of the ultraviolet ray irradiating device through the cooler, the cold air disinfected by the ultraviolet ray irradiating device can flow through the cooler and the fan in sequence, so that it can prevent the bacteria or the molds from adhering on the cooler and the fan in advance. In addition, in the air duct, because the ultraviolet ray irradiating device is installed at the location whose temperature is highest, the illuminating efficiency of the ultraviolet ray irradiating device can be increased.

Moreover, the ultraviolet rays from the ultraviolet ray irradiating device also irradiate the storage compartment and therefore, the storage compartment and the air duct can be also disinfected.

The invention further provides a refrigerator, comprising: a cooler, formed in the air duct, for use of a thermal exchange with the cooler to cool cold air in the air duct; a fan, for circulating the cold air cooled by the cooler, in the storage compartment; and an ultraviolet ray irradiating device. The ultraviolet rays from the ultraviolet ray irradiating device irradiate the storage compartment and the air duct. Therefore, both the storage compartment and the air duct can be also disinfected.

The above refrigerator further comprises a door for freely opening and closing an opening of the storage compartment. The ultraviolet rays from the ultraviolet ray irradiating device irradiate the storage compartment and the air duct according to a status whether the door has opened or closed the opening of the storage compartment. This prevents the ultraviolet rays from irradiating the user, so that the safety can be increased.

The above refrigerator further comprises a disinfection compartment divided from the storage compartment. The ultraviolet rays irradiating from the ultraviolet ray irradiating device to the storage compartment irradiate the disinfection compartment. By reflecting and diffusing the ultraviolet rays in the disinfection compartment, the ultraviolet rays can be concentratively irradiated, so as to achieve the disinfecting effect to such as breads or fresh foods. Additionally, by irradiating the ultraviolet rays to mushrooms, the vitamins in the mushrooms can be increased.

Furthermore, the refrigerator further comprises a plurality of special compartments adjacently formed in the storage compartment. At least one of the special compartments serves as the disinfection compartment, and at lease one surface of another special compartment covers one surface of the disinfection compartment. In this way, low temperature items can be cooled in the other special compartments, and the items in the disinfection compartment can be disinfected.

In the refrigerator, an inner surface of the disinfection compartment is made of a metal material. Therefore, it can prevent the inner surface of the disinfection compartment from damage due to the ultraviolet rays.

BRIEF DESCRIPTION OF THE DRAWINGS

While the specification concludes with claims particularly pointing out and distinctly claiming the subject matter which is regarded as the invention, the objects and features of the invention and further objects, features and advantages thereof will be better understood from the following description taken in connection with the accompanying drawings in which:

DESCRIPTION OF THE PREFERRED EMBODIMENT

Figure 1:
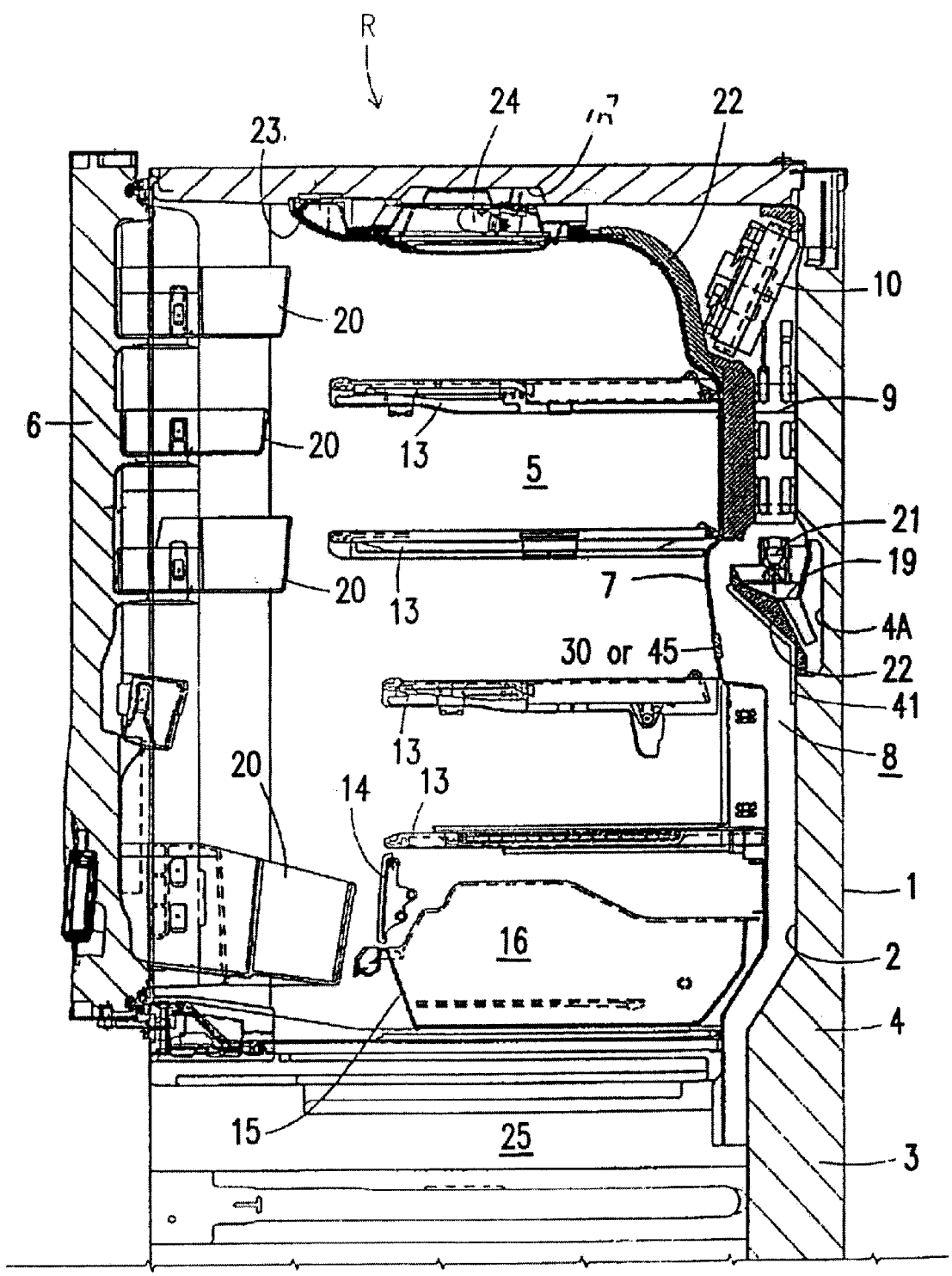
FIG. 1 is a side cross-sectional view, enlarging a portion of the refrigerator according to the invention.
Figure 2:
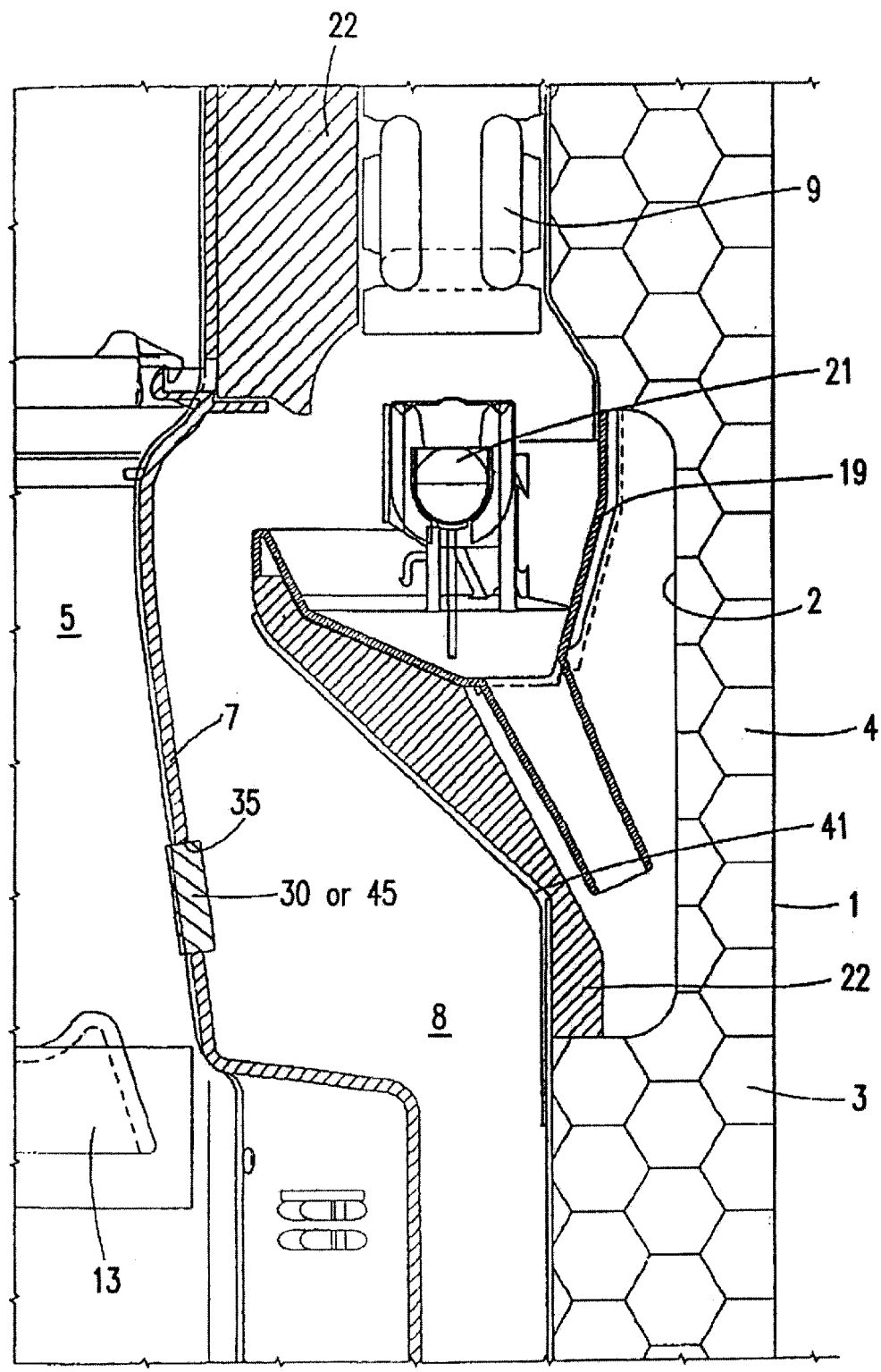
FIG. 2 is an enlarged cross-sectional view in FIG. 1.

The embodiment of the invention is described in detail in accordance with the attached drawings. FIG. 1 shows an enlarged side cross-sectional view of a portion of the refrigerator R of the invention. FIG. 2 is an enlarged view of a portion of FIG. 1. According to the invention, the refrigerator R is constituted of a thermal insulating housing 4. The thermal insulating housing 4 is formed by an in-situ foaming method to fill a thermal insulator 3 (for example, polyurethane foam) between an external housing 1, which is made of steel plate with an opening to the front end, and an interior housing 2 made of synthetic resin (such as ABS resin).

The interior of the thermal insulating housing 4 is divided into an upper part and a lower part by a dividing member (not shown) substantially arranged at the center of the thermal insulating housing 4. The upper part above the dividing member is maintained at a cold temperature (about +5° C.) and serves as a cold storage compartment 5. In addition, a temperature sensor 17 for detecting the temperature of the cold storage compartment is installed in the cold storage compartment 5 (cold temperature area). The temperature of the cold storage compartment 5 is controlled at a preset temperature by a microcomputer 18 (as a controlling device), which will be described in detail in following paragraphs.

Although the refrigerator under the dividing member is not shown in FIGS. 1 and 2, it is further divided into an upper portion and a lower portion by a thermal partition plate. For example, a vegetable compartment (not shown) is formed between the dividing member and the thermal partition plate (the upper portion) for storing foods such as vegetables that cannot be dry. Under the thermal partition plate (the lower portion), a freezing compartment (not shown) is formed for cooling down to a freezing temperature (about −20° C.).

Additionally, a mechanical room (not shown) is formed under the thermal insulating housing 4 and at the rear portion of the refrigerator. Inside the mechanical room, a compressor (FIG. 3) forming a refrigerating cycle as well-known as a cooler 9 (will be described in detail as follows), a condenser (not shown), and a blower for the condenser (not shown) etc. are installed.

Referring to FIG. 1, a thermal insulating door 6 capable of freely opening and closing is installed onto the front opening of the cold storage compartment 5. A plurality of door pockets 20 with various sizes is installed behind the thermal insulating door 6, i.e., facing the cold storage compartment 5. In addition, a door switch 12 (see FIG. 3), which serves as a detecting device for detecting whether the thermal insulating door 6 is open or not, is installed on the thermal insulating door 6 or on the edge of the front opening of the cold storage compartment 5. Other freezer compartments and the vegetable compartment can be freely opened and closed by thermal insulating doors of drawer type, for example.

A plurality of shelves 13 (made of synthetic resin, for example) is arranged from up to down in the cold storage compartment 5. A door 14 for a special room, which can be opened downwards, is installed at the front end of the lowest shelf 13. A drawer 15 capable of being drawn out is arranged at the lower portion of the cold storage compartment 5 and under the lowest shelf 13. Accordingly, a special compartment 16, surrounded by the drawer 15, the door 14, the lowest shelf 13 and a partition plate 7, is formed.

The partition plate 7 is formed in the cold storage compartment 5 from the top of the thermal insulating housing 4, across the back panel to the bottom of the cold storage compartment 5, so that the compartment 5 and thermal insulating housing 4 are separated by a preset gap. In this way, a cold-air duct 8 is formed between the cold storage compartment 5 and thermal insulating housing 4. A cooler 9 is vertically installed in the cold-air duct 8, and a fan 10 is installed above the cooler 9. In addition, a cold-air returning duct 25 for returning the cold air from the cold storage compartment 5 is installed inside the dividing member (not shown). The cold-air returning duct 25 is connected to the lower end of the cold-air duct 8. Moreover, the refrigerator has two coolers. One cooler for the cold temperature area is the cooler 9 in FIG. 1. The other cooler (not shown) for the freezing temperature area is arranged at the lower part of the refrigerator and behind the freezer compartment.

The fan 10 draws the cold air from the lower end of the cold-air duct 8 through the cold-air returning duct 25. After the cold air rises along the cold-air duct 8, the cold air is cooled by the cooler 9, and then blown from an outlet formed at the front end of the partition plate 7 that forms the ceiling of the cold storage compartment 5. In this way, the cold air is forced to circulate in the cold-air duct 8 and the cold storage compartment 5.

A drain dish 19 is arranged under the cooler 9 for receiving the drain water dropping from the cooler 9, and a drain heater 21 is arranged in the drain dish 19 for accelerating the vaporization of the received drain water. Furthermore, a recess 4A is formed on the back surface of the thermal insulating housing 4 for containing the drain dish 19. Additionally, in order to prevent the partition plate 7 from frosting and overcooling, thermal insulators 22 are arranged in the cold-air duct 8 near the drain dish 19, and arranged on the partition plate 7 located at the front sides of the fan 10 and cooler 9.

Referring to FIG. 1, an interior lamp 24 for illuminating the compartment 5 is installed in a recess 7A formed at the center portion of the partition plate 7 located at the ceiling.

On the other hand, an ultraviolet ray irradiating device 30 capable of irradiating ultraviolet rays is located on the partition plate 7 opposite to a position slightly below the drain dish 19, i.e., on the partition plate 7 located at a cold-air inflow side of the cooler 9 and separated from the cooler 9.

Figure 4:
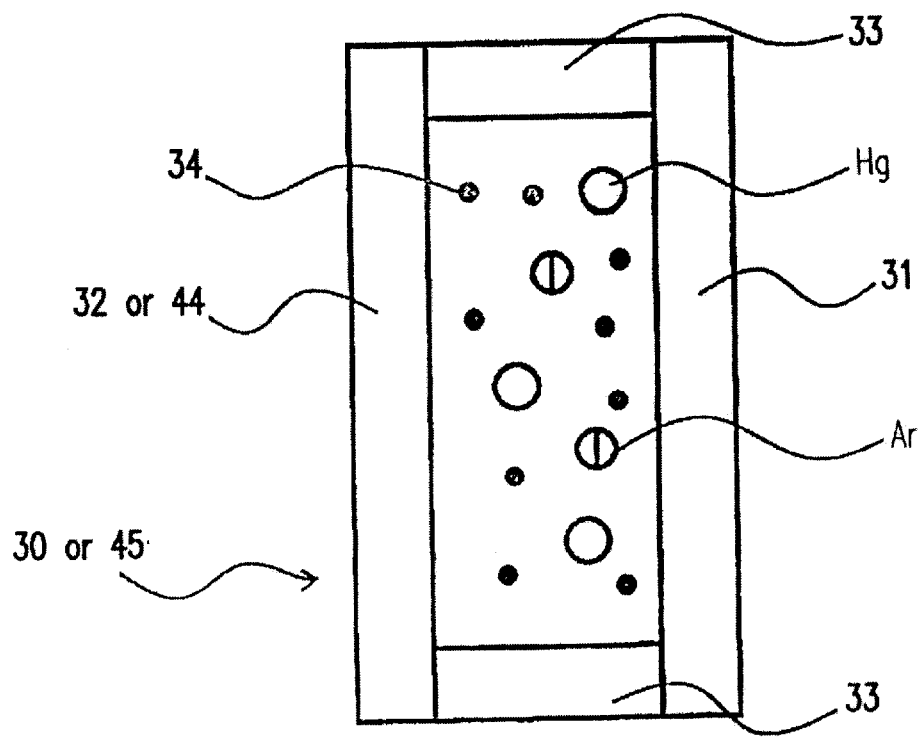
FIG. 4 is a cross-sectional view of the ultraviolet ray irradiating device.

The ultraviolet ray irradiating device 30 can be a plane-type lamp shown in FIG. 4, for example. In the embodiment, the ultraviolet ray irradiating device 30 is constituted of a discharging lamp. For example, ultraviolet ray irradiating device 30 consists of glass plates 31, 32 and glass 33, wherein the glass plates 31, 32 are made of synthetic quartz glass through which the ultraviolet rays with a wavelength of 254 nm can transmit, and the glass 33 are used for forming a sealed glass container so that the glass plates 31, 32 are separated by a preset distance. Discharging electrodes (not shown) are arranged in the glass 33 that form two sides of the sealed glass container, and the discharging electrodes are further connected to electrode leads (not shown). The inside of the sealed glass container is substantially vacuumed, and a little amount of mercury vapor (Hg) or a little amount of noble gas, such as Argon (Ar), for example, is sealed into the glass container.

As the electrode leads are connected to the alternative current (AC) power through wires (not shown) to discharge between the discharging electrodes, accelerated electrons 34 collide with the mercury vapor (Hg) or Argon molecules (Ar) so that the energy level of the electrons 34 changes from the ground state to the excited state. When the excited molecules or atoms return to the ground state, ultraviolet rays with a particular wavelength of each molecule irradiate and then transmit through the glass plates 31, 32, so that ultraviolet rays irradiate from the surfaces of the glass plates 31, 32.

Figure 5:
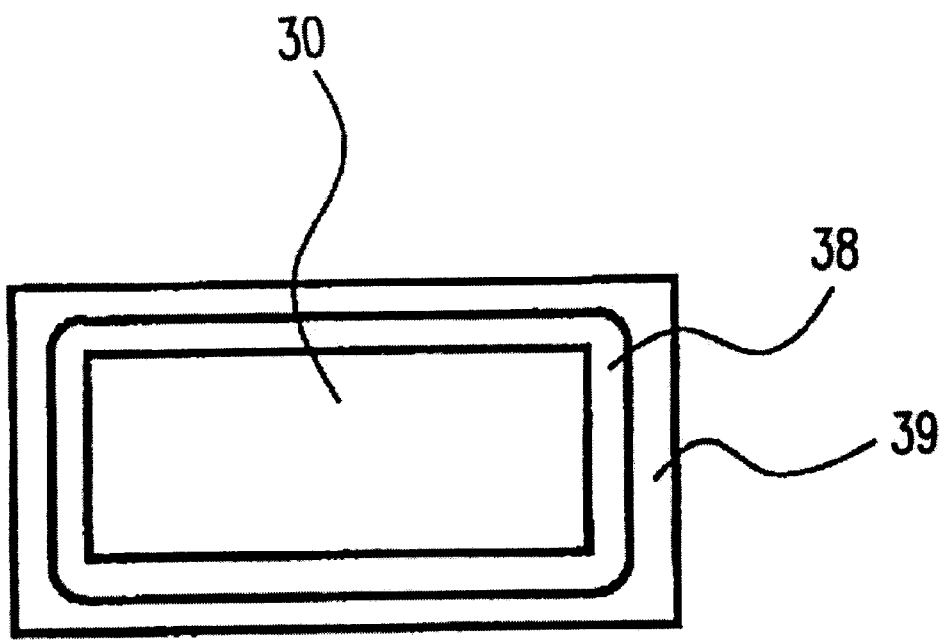
FIG. 5 is a front view of the ultraviolet ray irradiating device.
Figure 6:
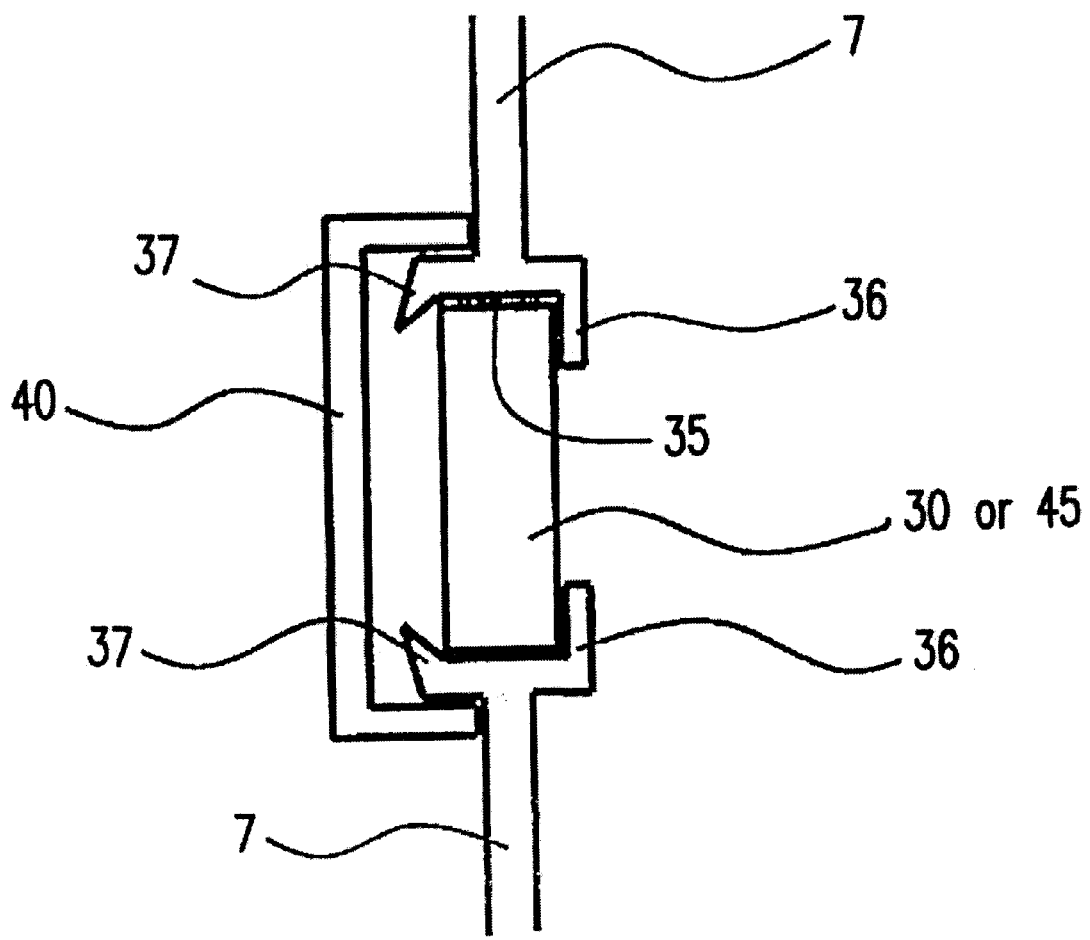
FIG. 6 a cross-sectional view when the ultraviolet ray irradiating device is installed on the partition plate.

As shown in FIGS. 5 and 6, the ultraviolet ray irradiating device 30 is installed on an opening 35 that is formed in advance at an installing position of the irradiating device 30 on the partition plate 7. Namely, a retainer 36 is formed on the upper and the lower edges (or on the left and the right edges, or the whole edges) of the opening 35 (formed on the partition plate 7) at the cold-air duct 8 side, to protrude into the cold-air duct 8, for supporting the ultraviolet ray irradiating device 30. In addition, a retainer 37, which is used for detachably engaging the ultraviolet ray irradiating device 30 from the compartment 5 side, is further formed on the upper and the lower edges (or on the left and right edges) of the opening 35 at the compartment 5 side.

As shown in FIG. 5, after a rubber material 38, for example, is assembled to tightly surround the top, the bottom, and two side surfaces of the ultraviolet ray irradiating device 30, an assembling plate 39 is mounted for holding the outer rim of the rubber material 38. In the status, the ultraviolet ray irradiating device 30 is assembled to the opening 35 on the partition plate 7. The assembling plate 39 is formed to be capable of detaching from the opening 35, and can be electrically conducted under a condition that the electrode leads (not shown) of the ultraviolet ray irradiating device 30 are coupled to the opening 35.

According to the aforementioned configuration, the ultraviolet ray irradiating device 30 can be easily detached from the compartment 5 side. Therefore, the maintenance of the ultraviolet ray irradiating device 30 is easy without disassembling the refrigerator to take out the ultraviolet ray irradiating device 30.

Furthermore, a cover 40, which is used to avoid the ultraviolet ray irradiating device 30 from being damaged and is made of a material capable of transmitting the ultraviolet rays, is assembled in front of the ultraviolet ray irradiating device 30 at the compartment 5 side. Additionally, the detailed installation is shown in FIG. 6.

The ultraviolet ray irradiating device 30 mounted on the assembling plate 39 is installed in such a way that the glass plates 31, 32, where the ultraviolet rays irradiate through, face the cold-air duct 8 and the cold storage compartment 5 respectively.

According to the above structure, as the compressor 11 (FIG. 3) of the cooling device and the fan 10 operate, the cold air cooled by the cooler 9 is drawn upwards by the fan 10 and then blown to the cold storage compartment 5 from the outlet 23. After cooling and circulating in the cold storage compartment 5, the cold air returns to the cold-air duct 8 via the cold-air returning duct 25. At this time, foods with bacteria and molds thereon might be stored in the cold storage compartment 5. The bacteria and the molds will be exfoliated from the foods due to the circulating cold air, and then return to the cold-air duct 8 together with the cold air.

By conducting the ultraviolet ray irradiating device 30 installed on the partition plate 7, the ultraviolet rays irradiate from the glass plate 31 of the ultraviolet ray irradiating device 30. Accordingly, the cold air returning to the cold-air duct 8, i.e., the circulating cold air, is irradiated by the ultraviolet rays.

In this way, various germs such as bacteria or molds etc in the returned cold air are killed by the ultraviolet rays. After the returned cold air is cleaned, the cleaned cold air is cooled by the cooler 9 and then blown to the cold storage compartment 5 from the outlet 23. Therefore, the cold air, in which the various germs are killed, circulates in the cold storage compartment 5 and the cold-air duct 8, to prevent germs from growing on the foods stored in the cold storage compartment 5 and to prevent foods from spoiling in advance.

Because the ultraviolet ray irradiating device 30 irradiates the ultraviolet rays directly to the cold storage compartment 5 through the glass plate 32, the foods stored in the cold storage compartment 5 can be directly disinfected.

The disinfection is performed not only to the foods in the cold storage compartment 5 and the cold air in the cold-air ducts, but also to the inside of the cold storage compartment 5 and the cold-air duct 8. The disinfection can be also performed to devices such as the fan 10 in the cold-air duct 8 or the drain dish 19 etc.

In this way, various germs such as the bacteria and the molds in the refrigerator R can be prevented from growing and malodor can be prevented.

According to the embodiment of the invention, the ultraviolet ray irradiating device 30 used in the refrigerator R is described that the glass plates 31, 32 uses the synthetic quartz glass capable of transmitting ultraviolet rays with a wavelength of 254 nm. However, a synthetic quartz glass capable of transmitting the ultraviolet rays with a wavelength to generate ozone (185 nm, for example) can be also used.

In this situation, because the ultraviolet rays to generate the ozone irradiate from the glass plates 31, 32, the ozone is generated in the cold-air duct 8 and the cold storage compartment 5, by which the disinfection and the deodorization can be performed.

In addition, light catalyst etc can be coated in the cold-air duct 8 where the ultraviolet rays from the ultraviolet ray irradiating device 30 can irradiate to. The cold air in the cold-air duct 8 can be deodorized by the light catalyst, and additionally, the germs adhered on the light catalyst become freshened so that the cold air in the cold-air duct 8 can be continuously deodorized.

Furthermore, the fan 10 is installed at a location opposite to the ultraviolet ray irradiating device 30 with the cooler 9 sandwiched therebetween, i.e., at an outflow side of the cooler 9 in the cold-air duct 8. Therefore, the cold air in which the various germs are killed by the ultraviolet ray irradiating device 30 can pass the cooler and the fan 10 in order, so as to prevent various germs from adhering to the cooler 9 and the fan 10.

Because the ultraviolet ray irradiating device 30 is assembled at a location where the temperature might be highest, the temperature of the ultraviolet ray irradiating device 30 is hardly reduced. Therefore, the efficiency and the performance of the ultraviolet ray irradiating device 30 can be increased.

In the embodiment of the invention, the ultraviolet ray irradiating device 30 is configured to a plane-type lamp to be able to comparatively save installation space in the limited space within the cold-air duct 8. Therefore, the space in the cold-air duct 8 can be efficiently utilized.

On the other hand, because the ultraviolet ray irradiating device 30 constituted of the plane-type lamp is installed on the opening 35 formed on the partition plate 7, the ultraviolet ray irradiating device 30 can be installed embedded in the partition plate 7. Furthermore, the installation space of the ultraviolet ray irradiating device 30 can be reduced so that the space efficiency of the cold-air duct 8 can be increased. In this way, because the storage volume of the cold storage compartment 5 will not be narrowed and the circulation of the cold air in the cold-air duct 8 and the cold storage compartment 5 will not be blocked, the cooling efficiency can be increased.

Figure 3:
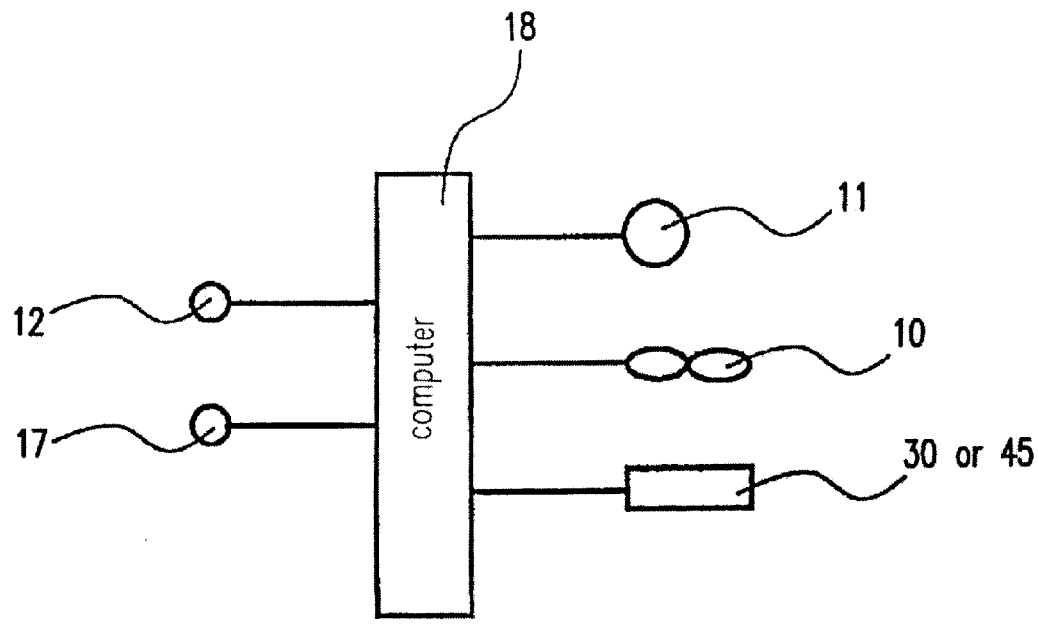
FIG. 3 is a block diagram showing a cooling device of the refrigerator of the invention.

The ultraviolet ray irradiating device 30 is electrically controlled by the microcomputer 18 (FIG. 3, the aforementioned controlling device). As shown in FIG. 3, the door switch 12 and the temperature sensor 17 are connected to the inputs of the microcomputer 18, and the compressor 11, the fan 10 and the ultraviolet ray irradiating device 30 are connected to the outputs of the microcomputer 18. Although not shown in FIG. 3, a device for setting the temperature in the refrigerator R and the interior lamp 24 etc can be also connected to the microcomputer 18.

In this way, when the microcomputer 18 detects by the door switch 12 the status that the thermal insulating door 6 has closed the opening of the cold storage compartment 5, the microcomputer controls to electrically conduct the ultraviolet ray irradiating device 30 and then ultraviolet rays irradiate the inside of the cold storage compartment 5 and the cold-air duct 8. Alternatively, when the microcomputer 18 detects by the door switch 12 the status that the thermal insulating door 6 has opened the opening of the cold storage compartment 5, the microcomputer controls to shutdown the electricity of the ultraviolet ray irradiating device 30 and then ultraviolet rays stop irradiating the insides of the cold storage compartment 5 and the cold-air duct 8.

Therefore, when the user of the refrigerator R opens the thermal insulating door 6, because ultraviolet rays from the ultraviolet ray irradiating device 30 do not irradiate the cold storage compartment 5, it can prevent the user from danger due to the direct irradiation of the ultraviolet rays in advance and the safety can be increased.

The door switch 12 also controls the operation of the fan 10. Namely, when detecting that the thermal insulating door 6 has closed the opening of the cold storage compartment 5, the door switch 12 can make the fan 10 operate; when detecting that the thermal insulating door 6 has opened the opening of the cold storage compartment 5, the door switch 12 can make the fan 10 stop. When detecting the door is open, the fan 10 is first stopped from operating. Except for this, the operation of the fan 10 is synchronized with the operation of the compressor 11 by a temperature control based on the temperature sensor 17.

Referring to FIGS. 1 and 2, a metal material 41 made of aluminum foil or stainless steel is adhered onto a location where ultraviolet rays from the ultraviolet ray irradiating device 30 irradiate, i.e., the location opposite to the installed location of the ultraviolet ray irradiating device 30 on the partition plate 7 in the cold-air duct 8, or the front surface of the inner housing 2 or the inner surface of the compartment 5 near the above location.

Accordingly, damages to the inner housing 2 made of the synthetic resin (such as ABS) that will be degraded due to the ultraviolet rays can be prevented from occurring. In addition, when the partition plate 7 is made of resin, the metal material can be also adhered on the partition plate 7 where the ultraviolet rays might irradiate, to obtain the same effect.

In addition, when the shelves 13 directly irradiated by the ultraviolet rays, the inner plate forming the thermal insulating door 6 facing the compartment 5 side, or the door pockets 20 etc are made of resin that might degrade due to the irradiation of the ultraviolet rays, the same metal material can be also adhered in the cold storage compartment 5 where the ultraviolet rays from the ultraviolet ray irradiating device 30 irradiate.

Figure 7:
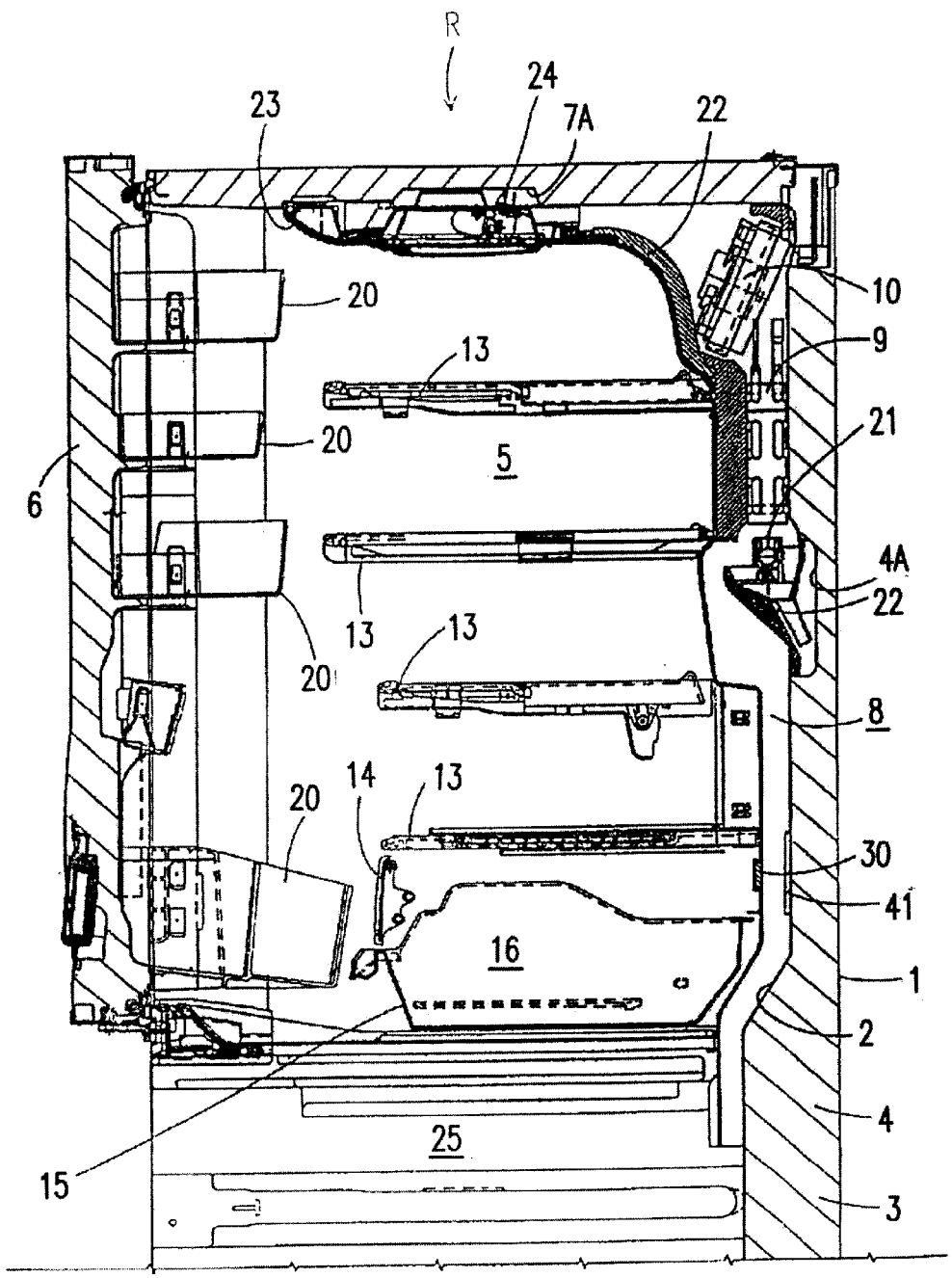
FIG. 7 is a side cross-sectional view, enlarging a portion of the refrigerator according to the invention.
Figure 8:
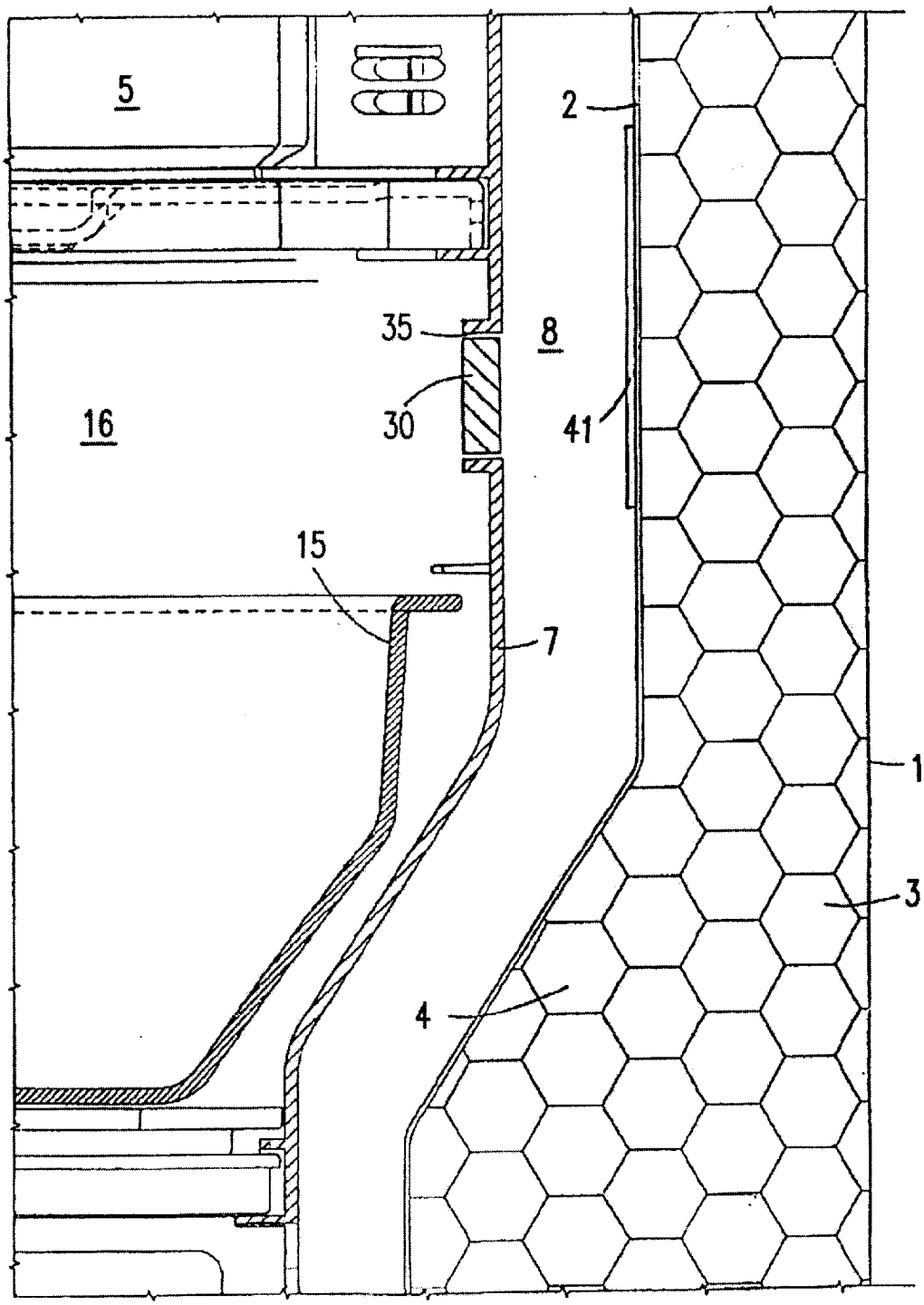
FIG. 8 is a enlarged cross-sectional view in FIG. 7.

Alternatively, as shown in FIGS. 7 and 8, the ultraviolet ray irradiating device 30 used in the embodiment can be installed on the partition plate 7 located behind the special compartment 16, and therefore the special compartment 16 can serve as a disinfection compartment. Furthermore, the opening 35 (see FIG. 8) is similarly formed on the partition plate 7 located behind the special compartment (the disinfection compartment) 16 and the ultraviolet ray irradiating device 30 can be detachably mounted to the opening 35 by the assembling plate 39.

In this situation, the drawer 15 arranged in the disinfection compartment 16 is made of a material that will not degrade due to the ultraviolet rays, i.e., a metal material such as stainless steel.

According to the above configuration, as the ultraviolet ray irradiating device 30 is electrically conducted, the ultraviolet rays irradiate from the glass plate 32 facing the inside of the disinfection compartment 16. The ultraviolet rays reflect and diffuse in the disinfection compartment 16 so that the ultraviolet rays can irradiate concentratively. In particular, if bread, fresh foods or eggs etc are stored in the disinfection compartment 16, the disinfecting effect for the foods, that are either unwrapped or are required to be particularly disinfected, is very excellent.

In addition, by irradiating the ultraviolet rays to the mushrooms etc, the vitamins retained in the mushrooms can be increased. As the ultraviolet rays irradiate the fruits etc, the fruit can become sweeter.

Because the glass plate 31 of the ultraviolet ray irradiating device 30 faces the inside of the cold-air duct 8, the cold air that circulates in the cold-air duct 8 can be disinfected. The metal material 41 made of the aluminum foil or the stainless steel can be adhered to the location where ultraviolet rays from the ultraviolet ray irradiating device 30 irradiate, i.e., the location opposite to the installed location of the ultraviolet ray irradiating device 30 on the partition plate 7 in the cold-air duct 8.

Figure 9:
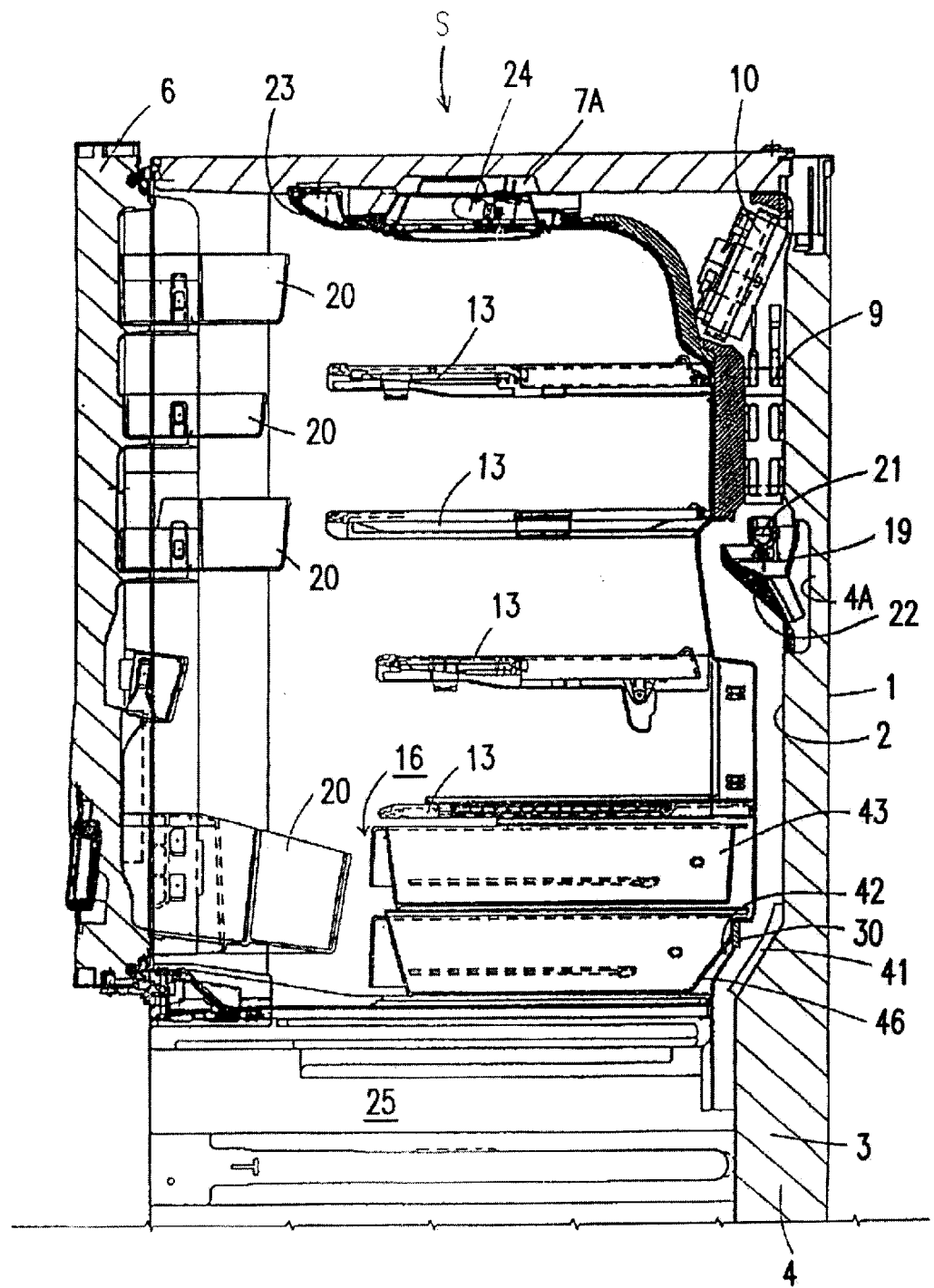
FIG. 9 is a side cross-sectional view, enlarging a portion of the refrigerator according to another embodiment of the invention.
Figure 10:
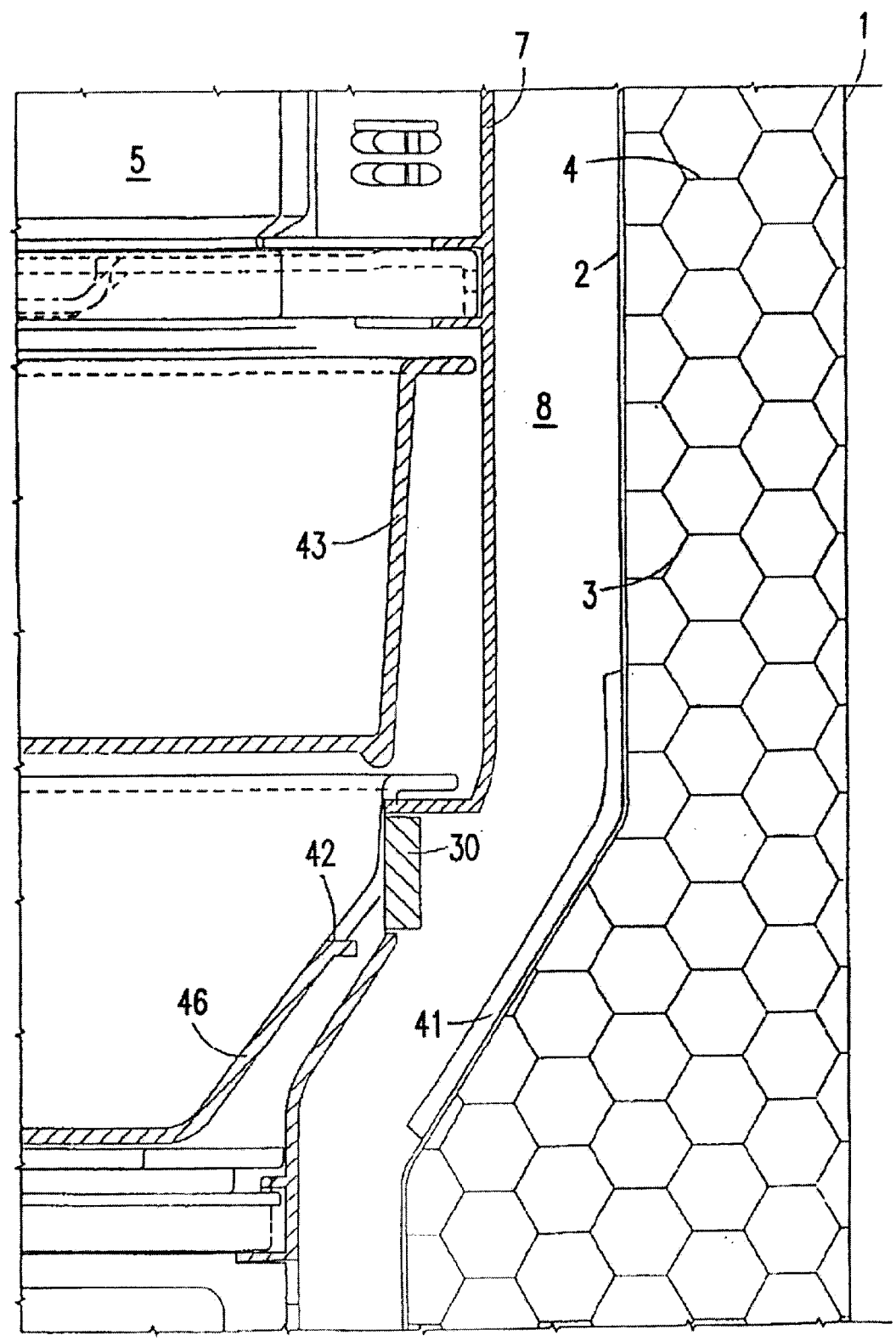
FIG. 10 is a enlarged cross-sectional view in FIG. 9.

FIGS. 9 and 10 describe another refrigerator S according to another embodiment of the invention. In addition to the structure mentioned in the above embodiment, the special compartment 16 of the refrigerator S of this embodiment is divided into two decks (upper and lower). Two drawers 43, 46 are arranged from top to bottom under the lowest shelf 13 in the cold storage compartment 5. Each of the two drawers 43, 46 has an upper opening and can be drawn out of the compartment 5. In this way, for example, a chilled compartment can be formed in the drawer 43 and a disinfection compartment can be formed in the drawer 46 inside the special compartment 16.

The drawers 43, 46 are hardly degraded by the ultraviolet rays and are respectively made of metal material such as stainless steel etc. The upper opening of the lower drawer 46 can be covered by the bottom of the upper drawer 43. Furthermore, an opening 42 is formed on the rear side of the lower drawer 46 for irradiating the ultraviolet rays from the ultraviolet ray irradiating device 30 to the inside of the drawer 46.

Similar to the previous embodiment, the ultraviolet ray irradiating device 30 can be installed on the partition plate 7 located behind the drawer 46. Furthermore, the opening 35 (see FIG. 10) is similarly formed on the partition plate 7 located behind the disinfection compartment 16 and the ultraviolet ray irradiating device 30 can be detachably mounted to the opening 35 by the assembling plate 39.

Accordingly, as the ultraviolet rays from the ultraviolet ray irradiating device 30 irradiate the inside of the drawer 46, the ultraviolet rays reflect and diffuse in the drawer 46, so that the ultraviolet rays can irradiate concentratively. In particular, if bread, fresh foods or eggs etc are stored in the disinfection compartment 16, the disinfecting effect for the foods, that are either unwrapped or are required to be particularly disinfected, is very excellent.

The disinfection can be performed on articles (such as foods) in the drawer 46 while articles of lower temperature are cooled in the drawer 43. In particular, even for meat composed of protein that is easily spoiled, the meat can be cooled in the drawer 43 separated by a portion that the ultraviolet rays do not transmit through, and the disinfection can be performed to vegetables etc in the drawer 46.

In this embodiment, the bottom the drawer 43 forming the chilled compartment in one portion of the special compartment 16 can cover the upper opening of the drawer 46 forming the disinfection compartment in another portion of the special compartment 16. Therefore, it is not necessary to assemble a cover for the drawer 46, so that the structure can be simplified. Additionally, this embodiment describes that the drawers 43, 46 are arranged top and bottom, but except for that, the chilled compartment and the disinfection compartment can be adjacently arranged in the special compartment 16.

Since the glass plate 31 of the ultraviolet ray irradiating device 30 faces the inside of the cold-air duct 8, the disinfection can be performed to the cold air that circulates in the cold-air duct 8. Moreover, a metal material 41 made of aluminum foil or stainless steel is adhered onto a location where ultraviolet rays from the ultraviolet ray irradiating device 30 irradiate, i.e., the location opposite to the installed location of the ultraviolet ray irradiating device 30 on the partition plate 7 in the cold-air duct 8, or the front surface of the inner housing 2 or the inner surface of the compartment 5 near the above location.

This embodiment utilizes the ultraviolet rays generated from the ultraviolet ray irradiating device 30 to irradiate the cold storage compartment 5. Therefore, kitchen accessories, such as the knife and the cutting board, can be put in the cold storage compartment 5 so that these accessories can be disinfected.

Next, an ultraviolet ray irradiating device 45 (also see FIGS. 1, 2, and 4) of the refrigerator R according to another embodiment is described. The ultraviolet ray irradiating device 45, for example, consists of a glass plates 31, 44 and glass 33 (see FIG. 4), wherein the glass plate 31 are made of synthetic quartz glass through which the ultraviolet rays with a wavelength of 254 nm can transmit, the glass plate 44 are made of a soda glass through which the visible light with a wavelength above 290 nm can transmit, and the glass 33 are used for forming a sealed glass container so that the glass plates 31, 32 are separated by a preset distance. Similar to the above ultraviolet ray irradiating device 30, discharging electrodes (not shown) and electrode leads (not shown) are connected, and the mercury vapor (Hg) or Argon (Ar) etc, is sealed into the glass container.

As the electrode leads are connected to the alternating current (AC) power through wires (not shown) to discharge between the discharging electrodes, accelerated electrons 34 collide with the mercury vapor (Hg) or Argon molecules (Ar) so that the energy level of the electrons 34 changes from the ground state to the excited state. When the excited molecules or atoms return to the ground state, ultraviolet rays with a particular wavelength of each molecule irradiate. At the side of the glass plate 31, the ultraviolet rays transmit through the glass plate 31 and irradiate from the surface of the glass plate 31. At the other side, when the ultraviolet rays are in contact with glass plate 44, visible light irradiates from the surface of the glass plate 44.

Similar to the above embodiments, when the ultraviolet ray irradiating device 45 is installed on the partition plate 7, through the rubber material 38 and the assembling plate 39, the ultraviolet ray irradiating device 45 is installed onto the opening 35 formed on the partition plate 7 that is separated from the cooler 9 and at the inflow side of the cooler 9. Therefore, the ultraviolet ray irradiating device 45 is installed in a manner such that the glass plate 31 irradiating the ultraviolet rays faces the cold-air duct 8 and the glass plate 44 faces the cold storage compartment 5.

At the cold-air duct 8 side, the ultraviolet ray irradiating device 45 irradiates ultraviolet rays from the glass plate 31, and therefore, the cold air circulating in the cold-air duct 8 or the devices in the cold-air duct 8 can be disinfected.

On the other hand, at the compartment 5 side, due to the irradiation of visible light from the glass plate 44, the ultraviolet ray irradiating device 45 can serve as an auxiliary lamp of the interior lamp 24 or as a main lamp, and has a function to indicate the illuminating status of the ultraviolet ray irradiating device 45. In addition, the interior design of the refrigerator can be more elegant.

By installing the ultraviolet ray irradiating device 45 onto the opening 35 on the partition plate 7, the surface capable of irradiating ultraviolet rays easily, i.e., the glass plate 31 facing the inside of the cold-air duct 8, and the surface capable of irradiating visible light, i.e., the glass plate 44 facing the inside of the compartment 5, are easily formed in a simple structure. The visible light and the ultraviolet rays can irradiate respectively to the cold storage compartment 5 and the cold-air duct 8. Therefore, the structure is very simple and the cost can be reduced.

A fluorescent material can be formed on the surface capable of irradiating the visible light from the ultraviolet ray irradiating device 45, i.e., on the glass plate 44. In this situation, when the ultraviolet rays created in the glass container are in contact with the fluorescent material on glass plate 44, the strength of the visible light irradiating from the glass plate 44 can be further increased, so that the illumination effect to the compartment 5 can be increased.

According to the invention, the refrigerator is divided into the storage compartment and the duct in the thermal insulating housing. The cold air for the use of the thermal exchange with the cooler in the duct circulates in the storage compartment by the fan. The refrigerator has an ultraviolet ray irradiating device with a surface capable of irradiating ultraviolet rays and a surface capable of irradiating visible light. By the ultraviolet ray irradiating device, the ultraviolet rays irradiate the duct and the visible light irradiates the storage compartment. In this way, the ultraviolet ray irradiating device can have a function of indicating the illuminating status in the storage compartment, and can disinfect the circulating cold air, the inner wall of the duct and the devices installed in the duct.

According to the invention, the refrigerator is divided into the storage compartment and the duct in the thermal insulating housing. The cold air for the use of the thermal exchange with the cooler in the duct circulates in the storage compartment by the fan. The refrigerator has an ultraviolet ray irradiating device capable of irradiating ultraviolet rays. The ultraviolet ray irradiating device is installed at the inflow side of cooler but separated from the cooler, so that the ultraviolet rays irradiate the duct by the ultraviolet ray irradiating device. In this way, the ultraviolet ray irradiating device is not exposed to the cold air cooled by the cooler, preventing the emitting efficiency of the ultraviolet ray irradiating device from being reduced.

According to the invention, the refrigerator is divided into the storage compartment and the duct in the thermal insulating housing. The cold air for the use of the thermal exchange with the cooler in the duct circulates in the storage compartment by the fan. The refrigerator has an ultraviolet ray irradiating device. Because the ultraviolet rays irradiate the storage compartment and the duct by the ultraviolet ray irradiating device, the storage compartment and the duct can be disinfected.

While the present invention has been described with a preferred embodiment, this description is not intended to limit our invention. Various modifications of the embodiment will be apparent to those skilled in the art. It is therefore contemplated that the appended claims will cover any such modifications or embodiments as fall within the What claimed is:

1. A refrigerator, comprising:
    a thermal insulating housing, formed in the refrigerator, and a storage compartment and an air duct being divided therein;
    a cooler, formed in the air duct, for use of a thermal exchange with the cooler to cool cold air in the air duct;
    a fan, for circulating the cold air cooled by the cooler, in the storage compartment;
    an ultraviolet ray irradiating device, having a first surface capable of irradiating ultraviolet rays and a second surface capable of irradiating visible light, wherein by the ultraviolet ray irradiating device, the ultraviolet rays irradiate the air duct and visible light irradiates the storage compartment.

2. The refrigerator of claim 1, wherein a fluorescent material is formed on the second surface capable of irradiating visible light.

3. The refrigerator of claim 2, further comprising a partition plate for dividing the storage compartment and the air duct, wherein the ultraviolet ray irradiating device is installed on the partition plate, so that the first surface capable of irradiating ultraviolet rays faces the air duct, and the second surface capable of irradiating visible light faces the storage room.

4. The refrigerator of claim 3, wherein the ultraviolet ray irradiating device is capable of detachably installing from one side of the storage compartment.

5. The refrigerator of claim 3, wherein the ultraviolet ray irradiating device is a plane-type lamp, and installed along a surface of the partition plate.

6. The refrigerator of claim 1, wherein a surface of the air duct, where the ultraviolet rays from the ultraviolet ray irradiating device irradiate thereon, is made of a metal material.

7. A refrigerator, comprising
    a thermal insulating housing, formed in the refrigerator, and a storage compartment and an air duct are divided therein;
    a cooler, formed in the air duct for use of a thermal exchange with the cooler to cool cold air in the air duct;
    a fan, for circulating the cold air cooled by the cooler, in the storage compartment;
    an ultraviolet ray irradiating device, capable of irradiating ultraviolet rays, wherein the ultraviolet ray irradiating device is installed at the inflow side of the cooler but separated from the cooler, so that the ultraviolet rays irradiate the air duct by the ultraviolet ray irradiating device; and
    a partition plate for dividing the storage compartment and the air duct, wherein the ultraviolet ray irradiating device is installed on the partition plate embedded in the partition plate.

8. The refrigerator of claim 7 wherein the fan is formed in the air duct and at an outflow side of the cooler.

9. The refrigerator of claim 7 wherein the ultraviolet ray irradiating device is a plane-type lamp.

10. The refrigerator of claim 7 wherein ultraviolet ray irradiating device has a first surface capable of irradiating ultraviolet rays and a second surface capable of irradiating visible light, wherein by the ultraviolet ray irradiating device, the ultraviolet rays irradiate the air duct and the visible light irradiates the storage compartment.

11. The refrigerator of claim 7 wherein the ultraviolet rays from the ultraviolet ray irradiating device also irradiate the storage compartment.

12. A refrigerator, comprising:
    a cooler, formed in an air duct, for use of a thermal exchange with the cooler to cool cold air in the air duct;
    a fan, for circulating the cold air cooled by the cooler in storage compartment;
    an ultraviolet ray irradiating device, wherein the ultraviolet rays from the ultraviolet ray irradiating device irradiate the storage compartment and the air duct; and
    a plurality of special compartments adjacently formed in the storage compartment, wherein at least one of the special compartment serves as the disinfection compartment, and at lease one surface of another special compartment covers one surface of the disinfection compartment.

13. The refrigerator of claim 12, further comprising a door for freely opening and closing an opening of the storage compartment, wherein the ultraviolet rays from the ultraviolet ray irradiating device irradiate the storage compartment and the air duct according to a status of whether the door has opened or closed the opening of the storage compartment.

14. The refrigerator of claim 12, wherein an inner surface of the storage compartment, where the ultraviolet rays from the ultraviolet ray irradiating device irradiate thereon, is made of a metal material.

15. The refrigerator of claim 12, wherein the disinfection compartment is divided from the storage compartment, and the ultraviolet rays irradiating from the ultraviolet ray irradiating device to the storage compartment irradiate the disinfection compartment.

16. The refrigerator of claim 15, wherein an inner surface of the disinfection compartment is made of a metal material.

17. The refrigerator of claim 12, wherein a surface of the air duct, where the ultraviolet rays from the ultraviolet ray irradiating device irradiate thereon, is made of a metal material.

18. The refrigerator of claim 12, wherein the ultraviolet ray irradiating device is a plane-type lamp.

19. A refrigerator, having a cold temperature area and a freezing temperature region, comprising:
    a first cooler, arranged at an upper portion from a middle of an innermost of the cold temperature area, for cooling the cold temperature area;
    a second cooler for cooling the freezing temperature region;
    an air duct, located at the innermost of the cold temperature area and below the first cooler, for returning cold air to the first cooler; and
    a discharging lamp, placed under the first cooler for creating ultraviolet rays and irradiating the ultraviolet rays to the air duct.

* * * * *